United States Patent
Teles et al.

(10) Patent No.: US 8,420,866 B2
(45) Date of Patent: Apr. 16, 2013

(54) PROCESS FOR PREPARING KETONES BY REACTING 1,1-DISUBSTITUTED OLEFINS WITH N₂O

(75) Inventors: Joaquim Henrique Teles, Otterstadt (DE); Michael Schelper, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 113 days.

(21) Appl. No.: 13/142,968

(22) PCT Filed: Dec. 14, 2009

(86) PCT No.: PCT/EP2009/067121
§ 371 (c)(1),
(2), (4) Date: Jun. 30, 2011

(87) PCT Pub. No.: WO2010/076182
PCT Pub. Date: Jul. 8, 2010

(65) Prior Publication Data
US 2011/0269996 A1    Nov. 3, 2011

(30) Foreign Application Priority Data

Dec. 30, 2008    (EP) ................................. 08173047

(51) Int. Cl.
*C07C 45/28* (2006.01)
*C07B 41/06* (2006.01)

(52) U.S. Cl.
USPC ........................................ 568/395; 568/398.8

(58) Field of Classification Search .................. 568/395, 568/398.8
See application file for complete search history.

(56) References Cited

U.S. PATENT DOCUMENTS

| | | | |
|---|---|---|---|
| 2,636,898 | A | 4/1953 | Buckley |
| 7,973,183 | B2 | 7/2011 | Goebbel et al. |
| 2005/0203316 | A1 | 9/2005 | Panov et al. |
| 2006/0106258 | A1 | 5/2006 | Panov et al. |
| 2006/0281952 | A1 | 12/2006 | Teles et al. |
| 2008/0255393 | A1 | 10/2008 | Teles et al. |
| 2008/0275276 | A1 | 11/2008 | Teles et al. |
| 2009/0227815 | A1 | 9/2009 | Teles et al. |
| 2010/0179352 | A1 | 7/2010 | Teles et al. |
| 2010/0180802 | A1 | 7/2010 | Gumlich et al. |
| 2011/0004025 | A1 | 1/2011 | Limbach et al. |
| 2011/0004032 | A1 | 1/2011 | Limbach et al. |
| 2011/0023538 | A1 | 2/2011 | Teles et al. |
| 2011/0023713 | A1 | 2/2011 | Rossler-Feigel et al. |
| 2011/0046401 | A1 | 2/2011 | Gumlich et al. |
| 2011/0087038 | A1 | 4/2011 | Teles et al. |
| 2011/0137077 | A1 | 6/2011 | Teles et al. |
| 2011/0152576 | A1 | 6/2011 | Teles et al. |

FOREIGN PATENT DOCUMENTS

| | | |
|---|---|---|
| DE | 10 2004 046 167 | 4/2006 |
| GB | 649 680 | 1/1951 |
| WO | 03 078370 | 9/2003 |
| WO | 03 078371 | 9/2003 |
| WO | 03 078372 | 9/2003 |
| WO | 03 078374 | 9/2003 |
| WO | 03 078375 | 9/2003 |
| WO | 2004 000777 | 12/2003 |
| WO | 2005 030689 | 4/2005 |
| WO | 2005 030690 | 4/2005 |
| WO | 2008 084046 | 7/2008 |
| WO | 2008 145656 | 12/2008 |
| WO | 2010 031745 | 3/2010 |

OTHER PUBLICATIONS

Starokon, E.V., et al., "Liquid Phase Oxidation of Alkenes with Nitrous Oxide to Carbonyl Compounds," Adv. Synth. Catal., vol. 346, pp. 268-274, (2004) XP 002321384.
Panov, G.I., et al., "Non-Catalytic Liquid Phase Oxidation of Alkenes with Nitrous Oxide. 1. Oxidation of Cyclohexene to Cyclohexanone," React. Kinet. Catal. Lett., vol. 76, No. 2, pp. 401-406, (2002).
Dubkov, K.A., et al., "Non-Catalytic Liquid Phase Oxidation of Alkenes with Nitrous Oxide. 2. Oxidation of Cyclopentene to Cyclopentanone," React. Kinet. Catal. Lett., vol. 77, No. 1, pp. 197-205, (2002).
International Search Report issued Apr. 12, 2010 in PCT/EP09/067121 filed Dec. 14, 2009.
U.S. Appl. No. 13/381,116, filed Dec. 28, 2011, Kunst, et al.

*Primary Examiner* — Sikarl Witherspoon
(74) *Attorney, Agent, or Firm* — Oblon, Spivak, McClelland, Maier & Neustadt, L.L.P.

(57) ABSTRACT

The present invention relates to a process for preparing a ketone, comprising the reaction of a composition (I) at least comprising a 1,1-disubstituted olefin, with a composition comprising dinitrogen monoxide, wherein the reaction is effected in the presence of a solvent which comprises at least one proton-donating functional group.

20 Claims, No Drawings

PROCESS FOR PREPARING KETONES BY REACTING 1,1-DISUBSTITUTED OLEFINS WITH N₂O

The present invention relates to a process for preparing a ketone, comprising the reaction of a composition (I) at least comprising a 1,1-disubstituted olefin, with a composition comprising dinitrogen monoxide, wherein the reaction is effected in the presence of a solvent which comprises at least one proton-donating functional group.

The oxidation of an olefinic compound to an aldehyde or a ketone by means of dinitrogen monoxide is, for example, described in GB 649,680 or the equivalent U.S. Pat. No. 2,636,898. Both documents disclose, in general terms, that the oxidation can in principle be effected in the presence of a suitable oxidation catalyst.

GB 649,680 describes the oxidation of olefins with dinitrogen monoxide to obtain, as the product, a mixture of a ketone and a cyclopropane derivative. It is further mentioned that these two products can be separated from one another by fractional distillation. However, a disadvantage is that a product mixture is obtained which has to be separated by a complicated purification.

The more recent scientific articles by G. I. Panov et al., "Non-Catalytic Liquid Phase Oxidation of Olefines with Nitrous Oxide. 1. Oxidation of Cyclohexene to Cyclohexanone", React. Kinet. Catal. Lett. Vol. 76, No. 2 (2002) p. 401-405, and K. A. Dubkov et al., "Non-Catalytic Liquid Phase Oxidation of Olefines with Nitrous Oxide. 2. Oxidation of Cyclopentene to Cyclopentanone", React. Kinet. Catal. Lett. Vol. 77, No. 1 (2002) p. 197-205, likewise describe oxidations of olefinic compounds with dinitrogen monoxide. A scientific article "Liquid Phase Oxidation of Olefines with Nitrous Oxide to Carbonyl Compounds" by E. V. Starokon et al. in *Adv. Synth. Catal.* 2004, 346, 268-274 includes a mechanistic study of the oxidation of olefins with dinitrogen monoxide in the liquid phase.

The synthesis of carbonyl compounds from olefins with dinitrogen monoxide is also disclosed in various international patent applications. For instance WO 03/078370 discloses a process for preparing carbonyl compounds from aliphatic olefins with dinitrogen monoxide. The reaction is performed at temperatures in the range from 20 to 350° C. and pressures of 0.01 to 100 atm. WO 03/078374 discloses a corresponding process for preparing cyclohexanone. According to WO 03/078372, cyclic ketones having 4 to 5 carbon atoms are prepared. According to WO 03/078375, cyclic ketones are prepared under these process conditions from cyclic olefins having 7 to 20 carbon atoms. WO 03/078371 discloses a process for preparing substituted ketones from substituted olefins. WO 04/000777 discloses a process for reacting di- and polyolefins with dinitrogen monoxide to give the corresponding carbonyl compounds.

WO 03/78370 describes the oxidation of olefins, generally with N₂O, to form ketones with the same carbon number. More particularly, the oxidation of 2-pentene without solvent and in the presence of various solvents (toluene, mesitylene, cyclohexane, cyclohexanone, acetonitrile and isobutanol) is described there. The experiments show that substantially identical results are achieved, irrespective of which solvent is used.

WO 2005/030690 and WO 2005/030689 describe processes for preparing cyclododecanone, wherein an oxidation with dinitrogen monoxide is effected in one process step. WO 2005/030690 describes a process for preparing cyclododecanone by oxidizing 1,5,9-cyclododecatriene (CDT) with N₂O to give cyclododeca-4,8-dienone, and then hydrogenating cyclododeca-4,8-dienone to cyclododecanone.

What is common to all processes is that the purity of the crude products is insufficient for some applications without additional purification. Especially cyclopropane derivatives are frequently present in the products obtained in large amounts.

This is problematic in that ketones are required in high purity for various applications. In these cases, a very complex purification, for example by multistage distillation and/or crystallization, is therefore necessary. As a result, these purification processes are inconvenient and costly.

It was therefore an object of the present invention to provide a process with which ketones can be obtained in high purity, in a simple manner and with a low level of complexity.

According to the invention, this object is achieved by a process for preparing a ketone, comprising the reaction of a composition (I) at least comprising a 1,1-disubstituted olefin, with a composition comprising dinitrogen monoxide, wherein the reaction is effected in the presence of a solvent which comprises at least one proton-donating functional group.

The process according to the invention can provide ketones with high purity, for example a purity of >99.5%. The process according to the invention is very selective, and so no further purification steps are needed and less product is lost.

In a preferred embodiment, the process according to the invention provides a ketone of the general formula (1)

from a 1,1-disubstituted olefin of the general formula (2)

where R1 and R2 are each independently selected from substituted and unsubstituted alkyl radicals having 1 to 20 carbon atoms, substituted and unsubstituted aryl radicals and where the R1 and R2 radicals may also be joined to one another and form a ring.

In a preferred embodiment, the present invention therefore relates to a process for preparing a ketone as described above, wherein the ketone is a ketone of the general formula (1)

and the 1,1-disubstituted olefin is an olefin of the general formula (2)

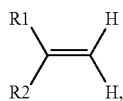
(2)

where R1 and R2 are each independently selected from substituted and unsubstituted alkyl radicals having 1 to 20 carbon atoms, substituted and unsubstituted aryl radicals and where the R1 and R2 radicals may also be joined to one another and form a ring.

According to the invention, the solvents used may be all substances which do not react with $N_2O$ under the reaction conditions and comprise a proton-donating functional group. Suitable examples are solvents which have at least one COOH group, solvents which have at least one OH group, or solvents which have at least one NH group.

In a further embodiment, the present invention therefore relates to a process for preparing a ketone as described above, wherein the solvent is selected from solvents consisting of the group of the solvents, which have at least one COOH group, the solvents which have at least one OH group, and the solvents which have at least one NH group.

Examples suitable in accordance with the invention of compounds having a COOH group are especially acetic acid, branched or unbranched, substituted or unsubstituted carboxylic acids having one or more carboxyl groups, and having up to 20 carbon atoms, aromatic carboxylic acids, and amino acids.

Examples suitable in accordance with the invention of compounds having an OH group are water, aliphatic alcohols having 1 to 20 carbon atoms, aliphatic diols having 2 to 20 carbon atoms, aliphatic triols having 3 to 20 carbon atoms, aliphatic polyols having 4 or more OH groups and 4 to 20 carbon atoms, phenol, and substituted phenols.

Examples suitable in accordance with the invention of compounds having an NH group are ammonia, hydrazine, primary and secondary aliphatic amines having 1 to 40 carbon atoms, aliphatic di- and polyamines having 2 to 20 carbon atoms, aromatic amines, and primary and secondary amides.

In a further embodiment, the present invention therefore relates to a process for preparing a ketone as described above, wherein the solvent is selected from the group consisting of carboxylic acids, amino acids, water, alcohols, ammonia, hydrazine, amines and amides.

Aliphatic alcohols suitable in accordance with the invention are, for example, methanol, ethanol, 1-propanol, 2-propanol, 1-butanol, 2-butanol, isobutanol, tert-butanol, 1-pentanol, 2-pentanol, isopentanol, tert-pentanol, cyclopentanol, 3-methyl-2-butanol, 1-hexanol, 2-hexanol, 3-hexanol, 2-methylpentanol-1, cyclohexanol, 1-heptanol, 1-octanol, 2-octanol, 2-ethylhexanol, 1-nonanol, n-nonanol, 1-decanol, 2-propylheptanol, 2-propyl-3-methyl-1-pentanol, 1-undecanol, 1-dodecanol, 2-butyloctanol, 2-butyl-3-methyl-1-heptanol, 1-tridecanol, n-tridecanol, 1-tetradecanol, 1-hexadecanol, 1-octadecanol, 1-icosanol, 2-methoxyethanol, 2-ethoxyethanol, 2-butoxyethanol, 2-phenoxyethanol, diethylene glycol monomethyl ether, triethylene glycol monomethyl ether, tetraethylene glycol monomethyl ether, 2-methoxy-1-propanol, 1-methoxy-2-propanol, dipropylene glycol monomethyl ether, tripropylene glycol monomethyl ether, 4-methoxy-1-butanol, 5-methoxy-1-pentanol, 6-methoxy-1-hexanol, and glyceryl carbonate.

Aliphatic diols suitable in accordance with the invention are, for example, ethylene glycol, 1,2-propanediol, 1,3-propanediol, 1,2-butanediol, 2,3-butanediol, 1,4-butanediol, 1,2-pentanediol, 1,5-pentanediol, 1,6-hexanediol, neopentyl glycol, 1,8-octanediol, 1,10-dodecanediol, 1,11-undecanediol, 1,12-dodecanediol, 1,13-tridecanediol, 1,14-tetradecanediol, 1,18-octadecanediol, diethylene glycol, triethylene glycol, tetraethylene glycol, dipropylene glycol, and tripropylene glycol.

Aliphatic triols suitable in accordance with the invention are, for example, glycerol, 1,2,4-butanetriol, trimethylolethane, trimethylolpropane, trimethylolbutane, diglycerol, 2-[2,2-bis(2-hydroxyethoxymethyl)butoxy]ethanol, triethanolamine, and tripropanolamine.

Aliphatic polyols which have at least 4 carbon atoms and are suitable in accordance with the invention are, for example, 1,2,3,4-butanetetrol, pentaerythritol, sorbitol, and 2-[3-(2-hydroxyethoxy)-2,2-bis(2-hydroxyethoxymethyl)propoxy] ethanol.

Phenols suitable in accordance with the invention are, for example, phenol, p-cresol, o-cresol, m-cresol, 2,6-xylenol, 2,4-xylenol, 2,5-xylenol, 2,3,6-trimethylphenol, mesitol, o-chlorophenol, m-chlorophenol, p-chlorophenol, 2-methoxyphenol, 4-methoxyphenol, alpha-naphthol, and beta-naphthol.

Carboxylic acids suitable in accordance with the invention are, for example, acetic acid, propionic acid, butyric acid, isobutyric acid, pivalic acid, valeric acid, 2-methylbutyric acid, isovaleric acid, hexanoic acid, 2-methylpentanoic acid, heptanoic acid, octanoic acid, 2-ethylhexanoic acid, 2-propylheptanoic acid, isononanoic acid, neodecanoic acid, stearic acid, benzoic acid, and o-toluic acid.

Primary and secondary aliphatic amines which have 1 to 40 carbon atoms and are suitable in accordance with the invention are, for example, methylamine, ethylamine, propylamine, isopropylamine, butylamine, isobutylamine, sec-butylamine, tert-butylamine, pentylamine, hexylamine, heptylamine, octylamine, 2-ethylhexylamine, 3,5,5-trimethylhexylamine, 2-propylheptylamine, dimethylamine, diethylamine, dipropylamine, diisopropylamine, dibutylamine, diisobutylamine, di-sec-butylamine, dipentylamine, dihexylamine, diheptylamine, dioctylamine, di-(2-ethylhexyl)amine, di-(3,5,5-trimethylhexyl)amine, di-(2-propylheptyl)amine, pyrrolidine, piperidine, and morpholine.

Aliphatic di- and polyamines which have 2 to 20 carbon atoms and are suitable in accordance with the invention are, for example, 1,2-ethylenediamine, 1,3-diaminopropane, N,N-dimethyl-1,3-diaminopropane, bis(3-dimethylaminopropyl)amine, bis(2-aminoethyl)amine, 1,4-diaminobutane, 1,5-diaminopentane, 1,6-diaminohexane, and piperidine.

Aromatic amines suitable in accordance with the invention are, for example, aniline, N-methylaniline, o-toluidine, m-toluidine, p-toluidine, and 2,6-xylylenediamine.

Primary and secondary amides suitable in accordance with the invention are, for example, formamide, acetamide, N-methylacetamide, pyrrolidone, caprolactam, and lauryllactam.

According to the invention, the solvents used are also compounds which simultaneously comprise at least one OH group and at least one NH group. Suitable examples in accordance with the invention are ethanolamine, 1-amino-2-propanol, 1-amino-2-methyl-2-propanol, 2-amino-2-methyl-1-propanol, 2-amino-2-methyl-1,3-propanediol, 2-amino-2-hydroxymethyl-1,3-propanediol, diethanolamine, or dipropanolamine.

It is likewise possible to use mixtures of two or more of the compounds mentioned.

According to the invention a composition (I) at least comprising a 1,1-disubstituted olefin is reacted with a composition comprising dinitrogen monoxide. It is possible in accordance with the invention to use any suitable 1,1-disubstituted olefin. Preference is given to using a composition (1) at least comprising a 1,1-disubstituted olefin of the general formula (2)

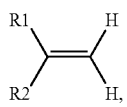

(2)

where R1 and R2 are each independently selected from substituted and unsubstituted alkyl radicals having 1 to 20 carbon atoms, and substituted and unsubstituted aryl radicals, and where the R1 and R2 radicals may also be joined to one another and form a ring.

More preferably, the 1,1-disubstituted olefin is an olefin of the general formula (2), and the R1 and R2 radicals are selected from substituted and unsubstituted alkyl radicals having 1 to 6 carbon atoms, and substituted and unsubstituted aryl radicals.

In a further embodiment, the present invention therefore relates to a process for preparing a ketone as described above, wherein the 1,1-disubstituted olefin is an olefin of the general formula (2) and the R1 and R2 radicals are selected from substituted and unsubstituted alkyl radicals having 1 to 6 carbon atoms and substituted and unsubstituted aryl radicals.

Suitable examples in accordance with the invention are isobutene, methylenecyclopropane, 2-methyl-1-butene, 2,4,4-trimethyl-1-pentene, 2,2,6,6-tetramethyl-4-methyleneheptane, alpha-polyisobutene, methylenecyclopentane, methylenecyclohexane, beta-pinene and 1,1-diphenylethene.

In a further embodiment, the present invention therefore relates to a process for preparing a ketone as described above, wherein the 1,1-disubstituted olefin is selected from the group consisting of isobutene, methylenecyclopropane, 2-methyl-1-butene, 2,4,4-trimethyl-1-pentene, 2,2,6,6-tetramethyl-4-methyleneheptane, alpha-polyisobutene, methylenecyclopentane, methylenecyclohexane, beta-pinene and 1,1-diphenylethene.

According to the invention, the composition (I) comprises the 1,1-disubstituted olefin typically in an amount of more than 80% by weight, preferably 85 to 99.999% by weight, especially 90 to 99.99% by weight, more preferably 92 to 99.9% by weight, for example 95 to 99.8% by weight. The composition (I) may, as well as the 1,1-disubstituted olefin typically comprise further compositions especially organic compounds.

The composition (I) at least comprising a 1,1-disubstituted olefin is reacted with a composition comprising dinitrogen monoxide. In the context of the present invention, dinitrogen monoxide can be used in pure form or in the form of a gas mixture comprising dinitrogen monoxide.

In principle, it is possible in the process according to the invention to use any gas mixture comprising dinitrogen monoxide. It is also possible in accordance with the invention to purify or to concentrate the gas mixture comprising dinitrogen monoxide before use in the reaction. A suitable purification process comprises, for example, the absorption of the gas mixture in an organic solvent or water, the desorption of the gas mixture from the laden organic solvent or the laden water, and the adjustment of the content of nitrogen oxides $NO_x$ in the gas mixture to at most 0.01 to 0.001% by volume based on the total volume of the gas mixture. Such a process is described, for example in DE 10 2004 046 167.8.

In principle, the gas mixture comprising dinitrogen monoxide used may originate from any desired source. More particularly, it is possible that the dinitrogen monoxide source used is the offgas of an industrial process.

The term "gas mixture" as used in the context of the present invention refers to a mixture of two or more compounds which are in the gaseous state at ambient pressure and ambient temperature. In the case of altered temperature or altered pressure, the gas mixture may also be in another state of matter, for example in liquid form, and is still referred to as a gas mixture in the context of the present invention.

In a further embodiment, the present invention therefore relates to a process for preparing a ketone as described above, wherein the dinitrogen monoxide source used is the offgas of an industrial process.

According to the invention, it is also possible to use a mixture of different offgases.

In a further preferred embodiment of the present invention, the at least one dinitrogen monoxide-comprising offgas originates from an adipic acid plant, a dodecanedioic acid plant, a hydroxylamine plant, a glyoxyl plant and/or a nitric acid plant, the latter in turn preferably being operated with at least one offgas of an adipic acid plant, a dodecanedioic acid plant, a glyoxyl plant or a hydroxylamine plant.

According to the invention, the gas mixture can be used in gaseous form. However, it is also possible first to treat the gas mixture comprising dinitrogen monoxide in such a way that the gas mixture is present in liquid or supercritical form and is then used. The gas mixture or dinitrogen monoxide can be liquefied by suitable selection of the pressure or of the temperature. It is equally possible in the context of the present invention to dissolve the gas mixture in a solvent.

According to the invention, the reaction conditions in the inventive reaction of the composition (I) at least comprising a 1,1-disubstituted olefin with the composition comprising dinitrogen monoxide may vary within wide ranges.

The temperatures in the inventive reaction of the composition (I) at least comprising a 1,1-disubstituted olefin with the composition comprising dinitrogen monoxide are preferably in the range from 140 to 350° C., further preferably in the range from 180 to 320° C. and more preferably in the range from 200 to 300° C.

In a further embodiment, the present invention therefore relates to a process for preparing a ketone as described above, wherein the reaction of a composition (I) at least comprising a 1,1-disubstituted olefin with a composition comprising dinitrogen monoxide is performed at a temperature in the range from 140 to 350° C.

It is possible to perform the reaction of the composition (I) at least comprising a 1,1-disubstituted olefin with the composition comprising dinitrogen monoxide at two or more temperatures or in two or more temperature ranges, each of which is within the limits specified above. Temperature changes in the course of the reaction can be conducted continuously or else discontinuously.

The pressures in the inventive reaction of the composition (I) at least comprising a 1,1-disubstituted olefin with the composition comprising dinitrogen monoxide are preferably higher than the autogenous pressure of the reactant or product mixture at the selected reaction temperature or the selected reaction temperatures. The pressures are preferably in the range from 1 to 1000 bar, further preferably in the range from 40 to 325 bar and more preferably in the range from 50 to 200 bar.

In a further embodiment, the present invention therefore relates to a process for preparing a ketone as described above, wherein the reaction of a composition (I) at least comprising a 1,1-disubstituted olefin with a composition comprising dinitrogen monoxide is performed at a pressure in the range from 1 to 1000 bar.

It is possible to perform the reaction of the composition (I) at least comprising a 1,1-disubstituted olefin with the composition comprising dinitrogen monoxide at two or more pressures or within two or more pressure ranges, each of which is within the limits specified above. Pressure changes in the course of the reaction can be conducted continuously or else discontinuously.

With regard to the reactors usable for the reaction of the composition (I) at least comprising a 1,1-disubstituted olefin with the composition comprising dinitrogen monoxide, there exist no particular restrictions. More particularly, the reaction can be effected in batchwise mode or in continuous mode. Accordingly, the reactors used may, for example, be at least one CSTR (Continuous Stirred Tank Reactor) with at least one internal and/or at least one external heat exchanger, at least one tubular reactor, at least one tube bundle reactor or at least one loop reactor. It is equally possible to configure at least one of these reactors such that it has at least two different zones. Such zones may differ, for example, in reaction conditions, for example the temperature or the pressure and/or in the geometry of the zone, for example, the volume or the cross section. When the reaction is performed in two or more reactors, it is possible to use two or more identical reactor types or at least two different reactor types.

Preference is given to performing the reaction of the composition (I) at least comprising a 1,1-disubstituted olefin with the composition comprising dinitrogen monoxide in a single reactor. For example, preference is given to the reaction in continuous mode.

The residence time of the reaction mixture in the at least one reactor in the reaction of the 1,1-disubstituted olefin with dinitrogen monoxide is generally in the range of up to 20 h, preferably in the range from 0.1 to 20 hours, further preferably in the range from 0.2 to 15 hours and especially preferably in the range from 0.25 to 10 h.

In the feed which is fed to the reaction of dinitrogen monoxide with the 1,1-disubstituted olefin, the molar ratio of dinitrogen monoxide to the 1,1-disubstituted olefin is generally in the range from 0.05 to 4, preferably in the range from 0.06 to 1, further preferably in the range from 0.07 to 0.5 and especially preferably in the range from 0.1 to 0.4.

The process according to the invention may further comprise further steps. Further steps may, for example be purification steps. Suitable purification steps are, for example, a distillated separation, especially a flash distillation. It is also possible in accordance with the invention that the process comprises a plurality of distillative separating steps, in order to remove unconverted reactants or solvent from the desired product. Unconverted reactants and/or solvent removed can preferably be recycled into the process according to the invention.

In a further embodiment, the present invention therefore relates to a process for preparing a ketone as described above, wherein the process, after the reaction of the composition (I) at least comprising a 1,1-disubstituted olefin with the composition comprising dinitrogen monoxide, has a further purification step.

The process according to the invention can be used to prepare ketones, which are very difficult to obtain by other routes in a simple one-stage synthesis. Such ketones can be used, for example, as synthesis units, or be used in other applications, for example, as specialty solvents, gasoline or diesel additives, etc.

The present invention will be illustrated in detail by examples hereinafter.

EXAMPLES

Example 1

Comparative Example

Oxidation of
2,2,6,6-tetramethyl-4-methyleneheptane
(triisobutylene) without Solvent at 260° C.

Triisobutylene (100 g) was introduced into a 300 ml autoclave, and the autoclave was closed and inertized with $N_2$. Triisobutylene was used as a technical grade mixture from Ineos Innovene (Cologne). The main components are (E/Z)-2,2,4,6,6-pentamethylhept-3-ene (~48%) and 2,2,6,6-tetramethyl-4-methyleneheptane (~34%), as well as other $C_{12}H_{24}$ hydrocarbons (~13% in total) and small proportions of oxygenates. The autoclave was purged three times with 50 bar of $N_2$ and then $N_2O$ was injected to cold pressure 50 bar. The stirrer was switched on and adjusted to 400 rpm, and then the autoclave was heated to target temperature (260° C.). After 24 h, the autoclave was cooled to room temperature and decompressed to ambient pressure, and the product was analyzed by GC.

The discharge obtained was: (E/Z)-2,2,4,6,6-pentamethylhept-3-ene (~35.3%) and 2,2,6,6-tetramethyl-4-methyleneheptane (30.5%), 4,4-dimethylpentan-2-one (4.3%), dineopentyl ketone (4.0%), 2-tert-butyl-1-(2,2-dimethylpropyl)-1-methyl-cyclopropane (1.6%), and further compounds.

The ratio between dineopentyl ketone and the cyclopropane derivative in this case was 2.5 g/g.

Example 2

Comparative Example

Oxidation of
2,2,6,6-tetramethyl-4-methyleneheptane
(triisobutylene) in Noninventive Solvent
(Cyclohexane) at 260° C.

Triisobutylene (10 g) and cyclohexane (90 g) were introduced into a 300 ml autoclave, and the autoclave was closed and inertized with $N_2$. Triisobutylene was used as a technical grade mixture from Ineos Innovene (Cologne). The main components are (E/Z)-2,2,4,6,6-pentamethylhept-3-ene (~48%) and 2,2,6,6-tetramethyl-4-methyleneheptane (~34%), as well as other $C_{12}H_{24}$ hydrocarbons (~13% in total) and small proportions of oxygenates. The autoclave was purged three times with 50 bar of $N_2$ and then $N_2O$ was injected to cold pressure 50 bar without stirrer movement. The stirrer was switched on and adjusted to 400 rpm, and then the autoclave was heated to target temperature (260° C.). After 24 h, the autoclave was cooled to room temperature and decompressed to ambient pressure, and the product was analyzed by GC.

The discharge obtained was: (without cyclohexane) (E/Z)-2,2,4,6,6-pentamethylhept-3-ene (~29.7%) and 2,2,6,6-tetramethyl-4-methyleneheptane (24.5%), 4,4-dimethylpentan- 2-one (3.2%), dineopentyl ketone (3.2%), 2-tert-butyl-1-(2,2-dimethyl-propyl)-1-methylcyclopropane (0.3%), and further compounds.

The ratio between dineopentyl ketone and the cyclopropane derivative in this case was 10.7 g/g. This result is better than that obtained in Example 1, but still unsatisfactory.

Example 3

Oxidation of 2,2,6,6-tetramethyl-4-methyleneheptane (triisobutylene) with Inventive Solvent (Methanol) at 260° C.

Triisobutylene (10 g) and methanol (90 g) were introduced into a 300 ml autoclave, and the autoclave was closed and inertized with $N_2$. Triisobutylene was used as a technical grade mixture from Ineos Innovene (Cologne). The main components are (E/Z)-2,2,4,6,6-pentamethylhept-3-ene (~48%) and 2,2,6,6-tetramethyl-4-methyleneheptane (~34%), as well as other $C_{12}H_{24}$ hydrocarbons (~13% in total) and small proportions of oxygenates. The autoclave was purged three times with 50 bar of $N_2$ and then $N_2O$ was injected without cold pressure 50 bar. The stirrer was switched on and adjusted to 400 rpm, and then the autoclave was heated to target temperature (260° C.). After 24 h, the autoclave was cooled to room temperature and decompressed to ambient pressure, and the product was analyzed by GC.

The discharge obtained was: (without methanol) (E/Z)-2,2,4,6,6-pentamethylhept-3-ene (~45.3%) and 2,2,6,6-tetramethyl-4-methyleneheptane (34.2%), 4,4-dimethylpentan-2-one (2.0%), dineopentyl ketone (3.6%), 2-tert-butyl-1-(2,2-dimethylpropyl)-1-methyl-cyclopropane (0.2%), and further compounds.

The ratio between dineopentyl ketone and the cyclopropane derivative in this case was 18 g/g and was thus significantly higher than in Examples 1 and 2.

Example 4

Comparative Example

Oxidation of 2,2,6,6-tetramethyl-4-methyleneheptane (triisobutylene) without Solvent at 290° C. (Elevated Temperature)

Triisobutylene (100 g) was introduced into a 300 ml autoclave, and the autoclave was closed and inertized with $N_2$. Triisobutylene was used as a technical grade mixture from Ineos Innovene (Cologne). The main components are (E/Z)-2,2,4,6,6-pentamethylhept-3-ene (~48%) and 2,2,6,6-tetramethyl-4-methyleneheptane (~34%), as well as other $C_{12}H_{24}$ hydrocarbons (~13% in total) and small proportions of oxygenates. The autoclave was purged three times with 50 bar of $N_2$ and then $N_2O$ was injected to cold pressure 50 bar without stirrer movement. The stirrer was switched on and adjusted to 400 rpm, and then the autoclave was heated to target temperature (290° C.). After 24 h, the autoclave was cooled to room temperature and decompressed to ambient pressure, and the product was analyzed by GC.

Discharge: (E/Z)-2,2,4,6,6-pentamethylhept-3-ene (32.2%) and 2,2,6,6-tetramethyl-4-methyleneheptane (30.4%), 4,4-dimethylpentan-2-one (7.12%), dineopentyl ketone (5.9%), 2-tert-butyl-1-(2,2-dimethylpropyl)-1-methylcyclopropane (2.6%), and further compounds.

The ratio between dineopentyl ketone and the cyclopropane derivative in this case was 2.26 g/g.

Example 5

Oxidation of 2,2,6,6-tetramethyl-4-methyleneheptane (triisobutylene) with Inventive Solvent (Methanol) at 290° C. (Elevated Temperature)

Triisobutylene (10 g) and methanol (90 g) were introduced into a 300 ml autoclave, and the autoclave was closed and inertized with $N_2$. Triisobutylene was used as a technical grade mixture from Ineos Innovene (Cologne). The main components are (E/Z)-2,2,4,6,6-pentamethylhept-3-ene (~48%) and 2,2,6,6-tetramethyl-4-methyleneheptane (~34%), as well as other $C_{12}H_{24}$ hydrocarbons (~13% in total) and small proportions of oxygenates. The autoclave was purged three times with 50 bar of $N_2$ and then $N_2O$ was injected to cold pressure 50 bar without stirrer movement. The stirrer was switched on and adjusted to 400 rpm, and then the autoclave was heated to target temperature (290° C.). After 24 h, the autoclave was cooled to room temperature and decompressed to ambient pressure, and the product was analyzed by GC.

Discharge (without methanol): (E/Z)-2,2,4,6,6-pentamethylhept-3-ene (15.3%) and 2,2,6,6-tetramethyl-4-methyleneheptane (28.4%), 4,4-dimethylpentan-2-one (10.0%), dineopentyl ketone (16.1%), 2-tea-butyl-1-(2,2-dimethylpropyl)-1-methylcyclopropane (0.2%), and further compounds.

The ratio between dineopentyl ketone and the cyclopropane derivative in this case was 80.5 g/g.

Example 6

Comparative Example

Oxidation of 2,4,4-trimethyl-1-pentene (alpha-diisobutylene) without Solvent alpha-diisobutylene (100 g) was introduced into a 300 ml autoclave, and the autoclave was closed and inertized with $N_2$. The autoclave was purged three times with 50 bar of $N_2$ and then $N_2O$ was injected to cold pressure 50 bar. The stirrer was switched on and adjusted to 400 rpm, then the autoclave was heated to target temperature (290° C.). After 24 h, the autoclave was cooled to room temperature, and decompressed to ambient pressure, and the product was analyzed by GC.

Discharge (without methanol): acetone (0.5%), alpha-diisobutylene (26.4%), methyl neopentyl ketone (25.1%), 2-tert-butyl-1,1-dimethylcyclopropane (10.4%) and further compounds.

The ratio between methyl neopentyl ketone and the cyclopropane derivative was 2.54 g/g.

Example 7

Oxidation of 2,4,4-trimethyl-1-pentene (alpha-diisobutylene) with Inventive Solvent (Methanol)

alpha-diisobutylene (10 g) and methanol (90 g) were introduced into a 300 ml autoclave, and the autoclave was closed and inertized with $N_2$. The autoclave was purged three times with 50 bar of $N_2$ and then $N_2O$ was injected to cold pressure 50 bar. The stirrer was switched on and adjusted to 400 rpm, then the autoclave was heated to target temperature (290° C.). After 24 h, the autoclave was cooled to room temperature, and decompressed to ambient pressure, and the product was analyzed by GC.

Discharge (without methanol): acetone (1.2%), alpha-diisobutylene (21.9%), methyl neopentyl ketone (32%), 2-tert-butyl-1,1-dimethylcyclopropane (0.4%) and further compounds.

The ratio between methyl neopentyl ketone and the cyclopropane derivative was 80 g/g.

The invention claimed is:

1. A process for preparing a ketone, comprising:
   reacting a composition (I) comprising a 1,1-disubstituted olefin, with a composition comprising dinitrogen monoxide,
   wherein the reacting is effected in the presence of a solvent which comprises at least one proton-donating functional group.

2. The process of claim 1, wherein the ketone is a ketone of formula (1)

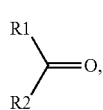

and the 1,1-disubstituted olefin is an olefin of formula (2)

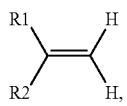

wherein R1 and R2 are each independently selected from the group consisting of a substituted alkyl radical having 1 to 20 carbon atoms, an unsubstituted alkyl radical having 1 to 20 carbon atoms, a substituted aryl radical, and an unsubstituted aryl radical, or R1 and R2 radicals are joined to one another and form a ring.

3. The process of claim 1, wherein the solvent is at least one selected from the group consisting of a solvent with at least one COOH group, a solvent with at least one OH group, and a solvent with at least one NH group.

4. The process of claim 1, wherein the solvent is at least one selected from the group consisting of a carboxylic acid, an amino acid, water, an alcohol, ammonia, hydrazine, an amine, and an amide.

5. The process of claim 1, wherein the 1,1-disubstituted olefin is an olefin of formula (2)

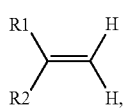

wherein R1 and R2 are selected from the group consisting of a substituted alkyl radical having 1 to 6 carbon atoms, an unsubstituted alkyl radical having 1 to 6 carbon atoms, a substituted aryl radical, and an unsubstituted aryl radical.

6. The process of claim 1, wherein the 1,1-disubstituted olefin is selected from the group consisting of isobutene, methylenecyclopropane, 2-methyl-1-butene, 2,4,4-trimethyl-1-pentene, 2,2,6,6-tetramethyl-4-methyleneheptane, alpha-polyisobutene, methylenecyclopentane, methylenecyclohexane, beta-pinene, and 1,1-diphenylethene.

7. The process of claim 1, wherein a source of the dinitrogen monoxide is an offgas of an industrial process.

8. The process of claim 1, wherein the reacting is performed at a pressure in a range from 1 to 1000 bar.

9. The process of claim 1, wherein the reacting is performed at a temperature in a range from 140 to 350° C.

10. The process of claim 9, further comprising, after the reacting, purifying a product of the reacting.

11. The process of claim 2, wherein the solvent is at least one selected from the group consisting of a solvent with at least one COOH group, a solvent with at least one OH group, and a solvent with at least one NH group.

12. The process of claim 2, wherein the solvent is at least one selected from the group consisting of a carboxylic acid, an amino acid, water, an alcohol, ammonia, hydrazine, an amine, and an amide.

13. The process of claim 3, wherein the solvent is at least one selected from the group consisting of a carboxylic acid, an amino acid, water, an alcohol, ammonia, hydrazine, an amine, and an amide.

14. The process of claim 2, wherein the 1,1-disubstituted olefin is an olefin of formula (2)

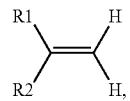

wherein R1 and R2 are selected from the group consisting of a substituted alkyl radical having 1 to 6 carbon atoms, an unsubstituted alkyl radical having 1 to 6 carbon atoms, a substituted aryl radical, and an unsubstituted aryl radical.

15. The process of claim 3, wherein the 1,1-disubstituted olefin is an olefin of formula (2)

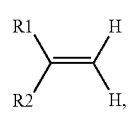

wherein R1 and R2 are selected from the group consisting of a substituted alkyl radical having 1 to 6 carbon atoms, an unsubstituted alkyl radical having 1 to 6 carbon atoms, a substituted aryl radical, and an unsubstituted aryl radical.

16. The process of claim 4, wherein the 1,1-disubstituted olefin is an olefin of formula (2)

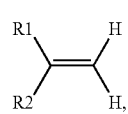

wherein R1 and R2 are selected from the group consisting of a substituted alkyl radical having 1 to 6 carbon atoms, an unsubstituted alkyl radical having 1 to 6 carbon atoms, a substituted aryl radical, and an unsubstituted aryl radical.

17. The process of claim 2, wherein the 1,1-disubstituted olefin is selected from the group consisting of isobutene, methylenecyclopropane, 2-methyl-1-butene, 2,4,4-trimethyl-1-pentene, 2,2,6,6-tetramethyl-4-methyleneheptane, alpha-polyisobutene, methylenecyclopentane, methylenecyclohexane, beta-pinene, and 1,1-diphenylethene.

18. The process of claim 3, wherein the 1,1-disubstituted olefin is selected from the group consisting of isobutene, methylenecyclopropane, 2-methyl-1-butene, 2,4,4-trimethyl-1-pentene, 2,2,6,6-tetramethyl-4-methyleneheptane, alpha-polyisobutene, methylenecyclopentane, methylenecyclohexane, beta-pinene, and 1,1-diphenylethene.

19. The process of claim 4, wherein the 1,1-disubstituted olefin is selected from the group consisting of isobutene, methylenecyclopropane, 2-methyl-1-butene, 2,4,4-trimethyl-1-pentene, 2,2,6,6-tetramethyl-4-methyleneheptane, alpha-polyisobutene, methylenecyclopentane, methylenecyclohexane, beta-pinene, and 1,1-diphenylethene.

20. The process of claim 5, wherein the 1,1-disubstituted olefin is selected from the group consisting of isobutene, methylenecyclopropane, 2-methyl-1-butene, 2,4,4-trimethyl-1-pentene, 2,2,6,6-tetramethyl-4-methyleneheptane, alpha-polyisobutene, methylenecyclopentane, methylenecyclohexane, beta-pinene, and 1,1-diphenylethene.

\* \* \* \* \*